United States Patent [19]

Di Maggio, Jr. et al.

[11] 4,274,359
[45] Jun. 23, 1981

[54] BIOLOGICAL SLIDE STAINING APPARATUS

[75] Inventors: Joseph P. Di Maggio, Jr., Bergenfield; Henry Eng, Clifton; Donald A. Ball, Warren; Kenneth J. Walenciak, Wayne, all of N.J.

[73] Assignee: A.J.P. Scientific, Inc., Clifton, N.J.

[21] Appl. No.: 897,884

[22] Filed: Apr. 19, 1978

[51] Int. Cl.² .................... B05C 11/12; B05C 13/02
[52] U.S. Cl. .......................................... 118/56; 118/64; 118/326; 118/500; 118/501
[58] Field of Search ................ 427/4; 118/64, 315, 118/56, 326, 500, 501; 422/50, 68

[56] References Cited

U.S. PATENT DOCUMENTS

| | | | |
|---|---|---|---|
| 2,400,315 | 5/1946 | Paasche | 118/64 |
| 3,053,223 | 9/1962 | Hensen et al. | 118/315 |

*Primary Examiner*—Bernard D. Pianalto
*Attorney, Agent, or Firm*—David A. Jackson

[57] ABSTRACT

An apparatus for the staining of a plurality of biological slides which comprises a slide support tray adapted to hold a plurality of slides in parallel position adjacent each other, a support tray rack assembly adapted to slidably receive said support tray, said rack assembly including a stain composition dispensing assembly providing a plurality of dispensing spigots, said spigots mounted on said rack assembly in overhead relation to said support tray when said support tray is fully received within said rack assembly, and means for removing excess stain composition and drying said slides, wherein said support tray is adapted for removable insertion and securement within said rack assembly. The apparatus of the present invention is contained within a central housing which also includes a single slide staining apparatus comprising a reciprocable slide support tray slidably connected to a separate rack assembly.

9 Claims, 12 Drawing Figures

BIOLOGICAL SLIDE STAINING APPARATUS

BACKGROUND OF THE INVENTION

The present invention relates to an apparatus for the staining of biological slides, and particularly to a slide staining apparatus which may automatically process a plurality of such slides.

In the biological arts, and particularly in the field of medical technology, the investigation of living tissues and fluids for structure and possible pathology has long proceeded with the aid of microscopic investigation. Specifically, samples of tissues and fluids have classically been placed upon small rectangular glass plates, known as slides, which are then placed under a microscope or similar magnifying device where visible structural characteristics may be viewed. In connection with microscopic investigations, the employment of staining compositions developed to aid in the identification process. At the inception, slides were manually treated and stained prior to viewing, however, particularly in the area of medical technology, the great numbers of slides that required staining for viewing in critical disease investigations, made it clear that the manual staining technique was inadequate. To this end, those in the art sought to develop methods and associated apparatus for the automatic staining of a plurality of slides.

At present, apparatus for the automated multiple staining of slides is available which employs a conveyor-type transporting arrangement, whereby the slides are placed on the conveyor and are sequentially indexed past stations for the dispensing of stain composition, buffer, and then rinse solution. The type of device thus described is presently employed in the area of blood sample evaluation, where the aforementioned critical parameters of time and volume are most pronounced. Though serving to alleviate somewhat the difficulties encountered in the employment of manual staining of the blood samples, the machine thus described suffers from certain defects of operation. Specifically, the slide is locked in position with the conveyor upon placement thereon and cannot be removed from the machine if, for some reason, it is desired to manually treat the particular sample in question. Secondly, the slides are stained in serial order and, frequently suffer from non-uniform staining due to excess dispensing of the stain composition components at the respective stations. Further, the mechanism comprising the conveyor frequently causes jamming of slides with resulting delays in slide movement, which itself may contribute to overstaining of a particular sample, and which generally delays the staining process for all slides presently on the machine.

In addition to the above, the need has developed for the semi-automatic staining of a single slide, without resorting to fully manual staining techniques, so that the benefits of a premeasured amount of stain composition may be gained in conjunction with the ability to process a single slide. Presently, no device is known which possesses this latter capability, and, in sum, it is to the satisfaction of all of the foregoing deficiencies in the prior art that the present invention is directed.

SUMMARY OF THE INVENTION

In accordance with the present invention, an apparatus for staining biological slides is disclosed which comprises a slide support tray adapted to hold a plurality of slides in parallel position adjacent to each other, a support tray rack assembly adapted to slidably receive said support tray, said rack assembly including a biological slide staining composition dispensing assembly providing a plurality of dispensing spigots, said spigots mounted on said rack assembly so as to reside in overhead relation to said support tray when said support tray is fully received within said rack assembly, and means for removing excess stain composition and drying said slides, where said support tray is adapted for removable insertion and securement within said rack assembly. The slide support tray of the present invention comprises a generally rectangular outer frame containing an aperture within which nests an inner shelf member, which shelf member is adapted to support a plurality of biological slides in parallel relation to each other, and is further capable of pivoting upward in relation to said frame in order to facilitate the rapid drain off of excess stain composition from the slides.

The staining apparatus of the present invention further includes a single slide staining assembly which provides a slide tray permanently affixed thereto, said slide tray adapted to reciprocate a single slide into position adjacent the stain composition dispensing spigots provided therewith.

The apparatus of the present invention is characterized by ease of operation and accuracy of staining, as the slide samples are subjected to the various staining sequences while at one station. Thus, all of the dispensing spigots for the respective components of the staining solutions are located together above the respective slides, rather than at spaced locations or stations. Further, employment of manual conveyance of the slides to the staining station in the apparatus of the present invention eliminates the possibility of jamming or other malfunction which frequently leads to inaccuracies in staining and damage to the slide samples.

A further feature of the present invention resides in the provision of an individual slide staining station which permits the preparation of an individual or single slide independent of the automated staining of a plurality of slides. The individual slide station is characterized by the provision of separate structures for the various components thereof and is associated with the multiple slide staining apparatus only in the reliance on the common reservoirs of slide staining solution.

Accordingly, it is a principal object of the present invention to provide an apparatus for the staining of biological slide samples which is easily and rapidly operated with reduced incidence of failure.

It is a further object of the present invention to provide a slide staining apparatus as aforesaid which employs manual slide mounting and removal without detriment to reduced staining time.

It is a yet further object of the present invention to provide a slide staining apparatus as aforesaid which facilitates the simultaneous, independent staining of a plurality of slides and a single slide.

Other objects and advantages will become apparent to those skilled in the art from a review of the ensuing description which proceeds with reference to the following accompanying drawings.

DETAILED DESCRIPTION OF THE INVENTION

Figure 1:
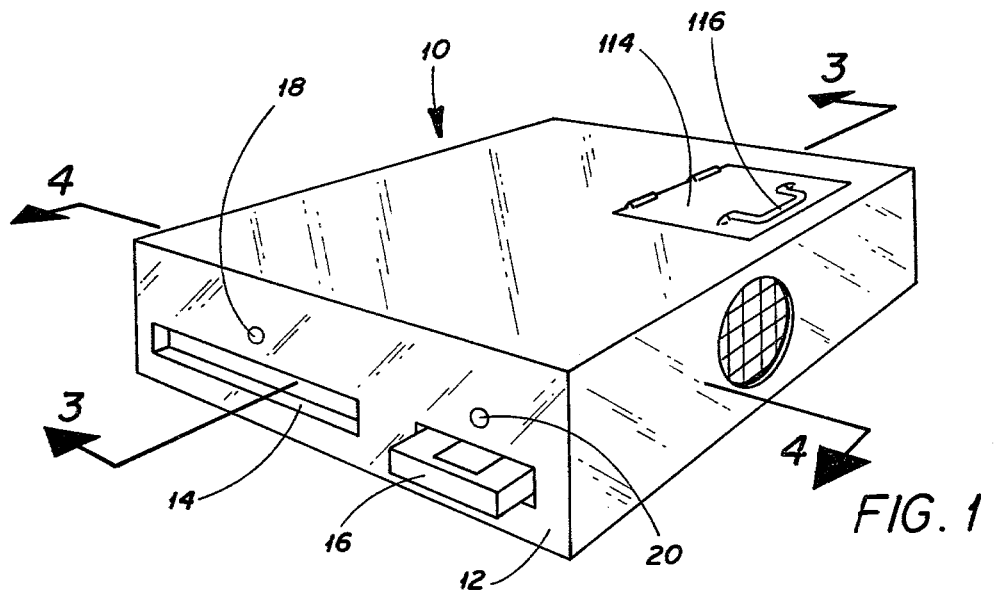
FIG. 1 is a perspective view of the outer appearance of the apparatus of the present invention.

Referring to the drawings, wherein like numerals designate like parts, FIG. 1 illustrates the outer appearance of the slide staining apparatus of the present invention. Thus, apparatus 10 is generally rectangular in shape and provides, at the front face 12, a large rectangular mouth 14 which comprises the point of insertion of a slide support tray as will be further described below. Adjacent mouth 14, reciprocable single slide tray 16 is shown which resides in association with a separate slide support rack for the simultaneous staining of a single slide. The apparatus associated with single slide tray 16 will be described in greater detail later on.

Referring further to FIG. 1, indicator lights 18 and 20 are shown which, respectively, signal the operation of the multiple and single slide staining apparatus. Further, when the slide staining procedure is terminated the indicator lights will extinguish to advise that the staining procedure is over.

Figure 2:
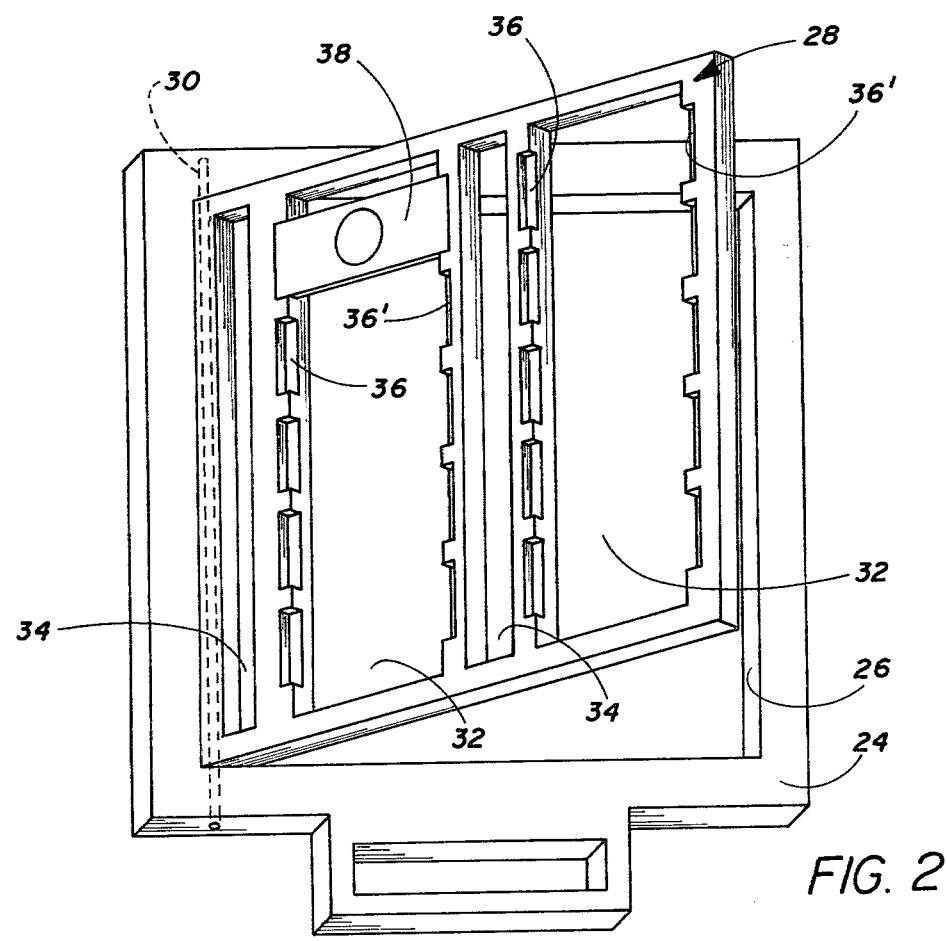
FIG. 2 is a top perspective view partly in phantom showing the slide support tray of the present invention in one of its operative positions.

Referrring now to FIG. 2, the slide support tray 22 employed in accordance with the multiple slide staining section of the present invention is shown in perspective to illustrate the manner of operation. Thus, tray 22 is seen to comprise a generally rectangular outer tray frame 24 which defines a generally rectangular aperture 26 within which a centrally located rectangular slide shelf 28 may be situated. As shown in phantom, slide shelf 28 is adapted for pivoting movement in relation to frame 24 by the placement of axle 30 journaled through both shelf 28 and frame 24 as illustrated. As will be described hereinbelow, the pivoting movement of slide shelf 28 enhances the drying of the slide as it facilitates the runoff of excess stain composition.

Slide shelf 28 is further provided with paired, parallel rectangular openings comprising major openings 32 and minor openings 34, openings 32 and 34 situated in alternating relationship to each other. Openings 32 are provided with paired recesses 36 and 36' which comprise seats for situation of the slides therein. Thus, before inserting support tray 22 into mouth 14, one places a plurality of slides such as slide 38 in communication with paired recesses 36 and 36', where they will reside until the staining process is completed.

Minor openings 34 are provided in position adjacent major openings 32 so that when slide shelf 28 is placed in the tilted position as shown, excess stain composition will run off slide 38 and will drop through minor openings 34. As will be shown hereinafter, the base of the apparatus of the present invention serves as a drain or sump to collect all excess slide stain composition removed in this manner.

Figure 3:
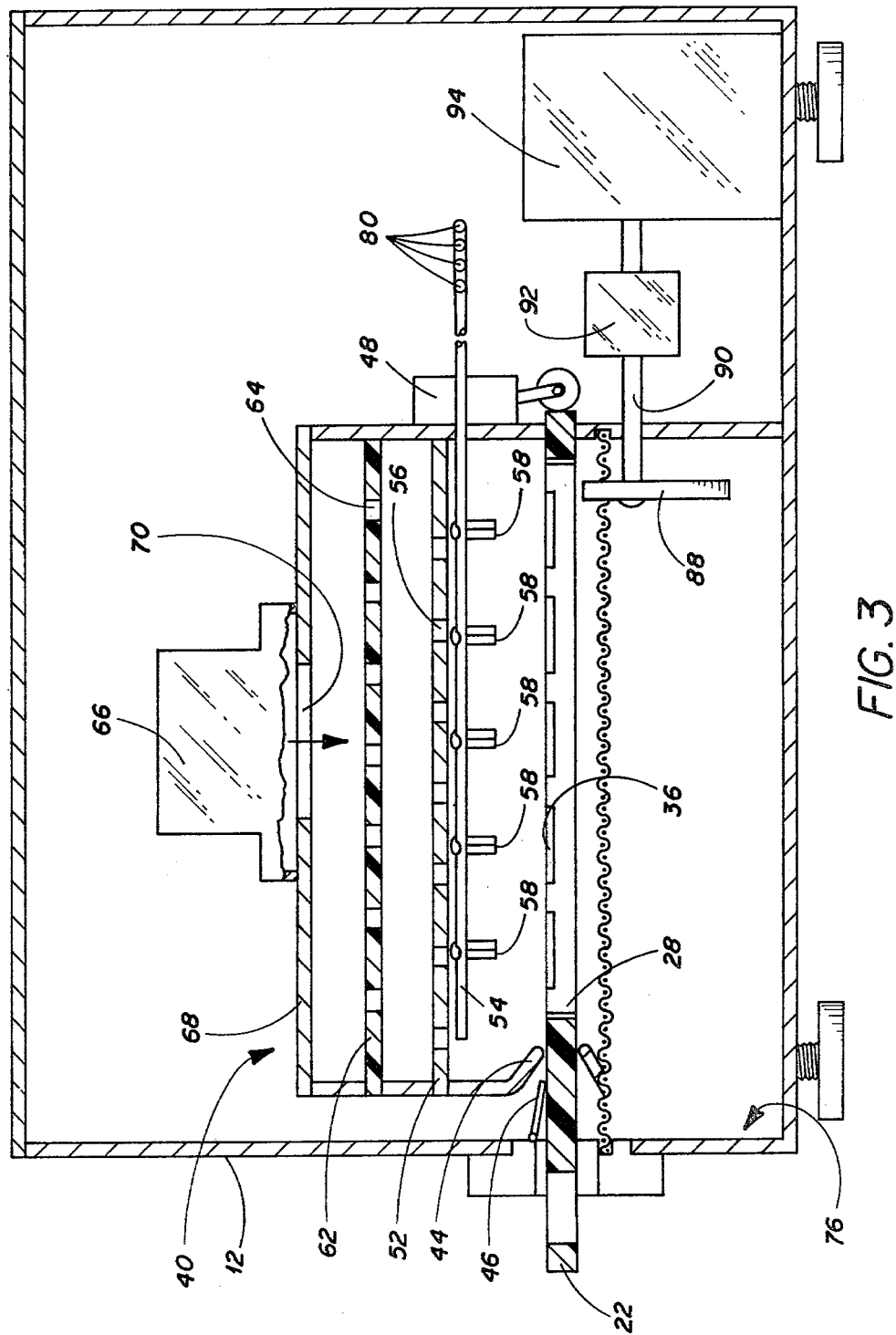
FIG. 3 is a side sectional, partly schematic view taken through line 3—3 of FIG. 1 further illustrating the apparatus of the present invention.
Figure 4:
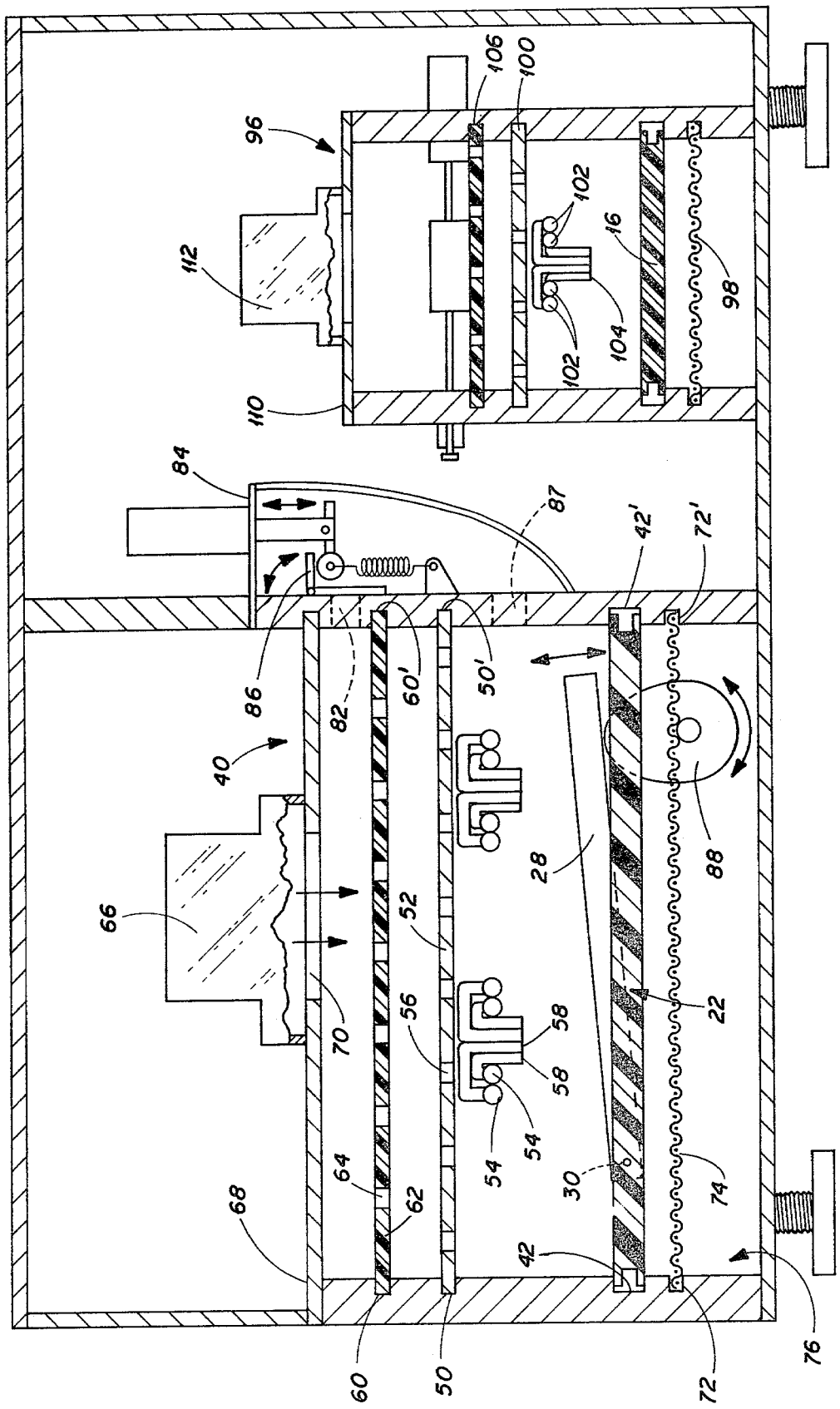
FIG. 4 is a front sectional view of the apparatus of FIG. 1 taken through 4—4.

In the employment of the apparatus of the present invention to stain a plurality of slides simultaneously, slide support tray 22 is appropriately loaded with a plurality of biological slide samples placed within recesses 36 and 36' so that the samples reside in upward facing direction. After loading, slide support tray 22 is then inserted into mouth 14 of the apparatus and is then pushed as far as possible until residing within the positions illustrated in FIGS. 3 and 4. Thus, in FIG. 3, slide support tray 22 can be seen to reside within support tray rack assembly 40 within tracks 42 and 42' as illustrated in FIG. 4. Rack assembly 40 comprises an essentially rectangular structure having a plurality of tracks such as 42 and 42' for the support of various parallel structures described hereinafter. The opening of rack assembly 40 provided for the insertion of slide support tray 22 possesses a beveled entrance 44 which assists in guiding slide support tray 22 on insertion. As illustrated in FIG. 3, front facing 12 may be provided at mouth 14 with a pivotable door 46 which moves upward and out of the way of slide tray 22 on insertion, but is spring loaded and adapted to reside in the closed position parallel with facing 12 when the slide tray is removed. Also, pressure switch 48 is provided at the rear of rack assembly 40 to signal the commencement of the staining sequence when slide tray 22 is fully inserted and abuts thereagainst.

Referring to FIG. 4, rack assembly 40 can be seen to comprise an essentially rectangular structure defining a plurality of spaced apart, parallel tracks for the insertion of and in support of a plurality of structures to be located in overhead relation to slide support tray 22. Specifically, tracks 50 and 50' are provided directly above tracks 42 and 42' to engage diffuser plate 52 which in turn provides support to stain composition dispensing manifolds 54. Diffuser plate 52 is provided with a plurality of perforations or apertures 56 which serve to permit air flow therethrough to assist in drying slides 38 after the application of the slide staining compositions. Dispensing manifolds 54 can be seen to comprise essentially cylindrical structures which serve as the final conduits of the respective components of the staining compositions in a manner to be described later on. Referring to FIG. 4, manifolds 54 are provided in two banks of four manifolds each corresponding in number to the components of the stain compositions sequentially applied to the slides. Each of the manifolds 54 has provided thereon a plurality of slide composition dispensing spigots 58 which emanate from the uppermost surfaces of the manifolds 54 and turn downward to direct their respective compositions on the slides. As can be seen in FIG. 3, spigots 58 are provided in correspondence to the number of slides provided on each bank, which, as illustrated herein, comprise five slides per bank, for a total of ten slides which may be seated on slide tray 22 and simultaneously stained upon insertion within rack assembly 40.

Referring further to FIG. 4, a third pair of tracks 60 and 60' are provided above tracks 50 and 50' to receive baffle plate 62, which serves in a manner similar to diffuser plate 52 to permit air to circulate downward and over slides 38 after excess stain composition has been removed. Thus, baffle plate 62 also defines a plurality of baffle plate apertures 64 which permit the air to pass therethrough.

Both diffuser plate 52 and baffle plate 62 are provided for use in conjunction with a blower 66 which is mounted on a support plate 68 located above baffle plate 62 and is adapted to direct a blast of air downward through support plate opening 70 toward the slides 38 to hasten the removal of excess stain composition therefrom.

Referring again to FIG. 4, one further set of tracks 72 are provided below slide support tray 22 to house screen 76 which is provided to catch a slide 38 should it slip out of position on slide shelf 28 when shelf 28 is tilted in the manner illustrated in the Figure, during the drain-off sequence. Rack assembly 40 defines at the bottom thereof a sump or drain 76 for the purpose of retaining stain composition removed from slides 38 during the draining and dying sequence described hereinafter.

Figure 5:
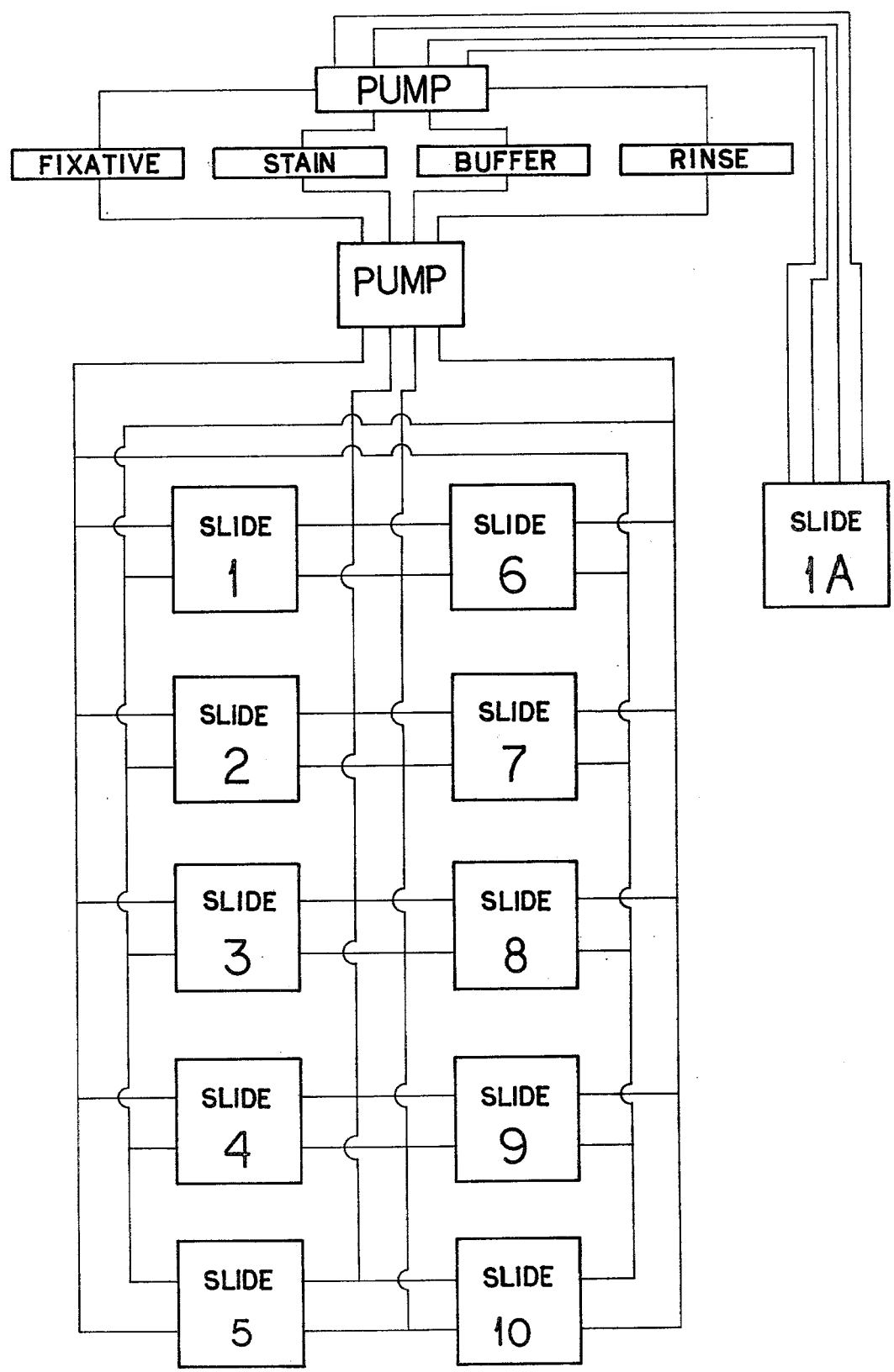
FIG. 5 is a schematic flow diagram illustrating the dispensing means of the apparatus of the present invention.
Figure 6:
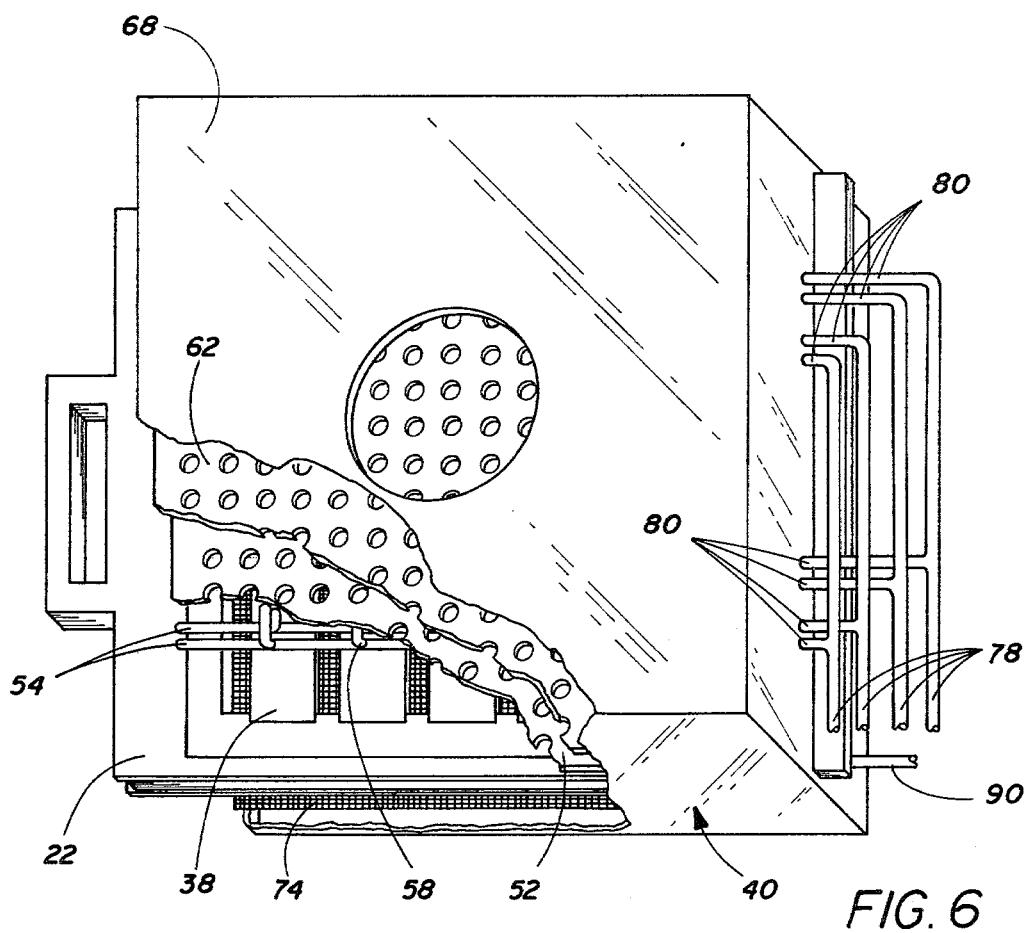
FIG. 6 is perspective view partly broken showing yet another view of the present invention.
Figure 7:
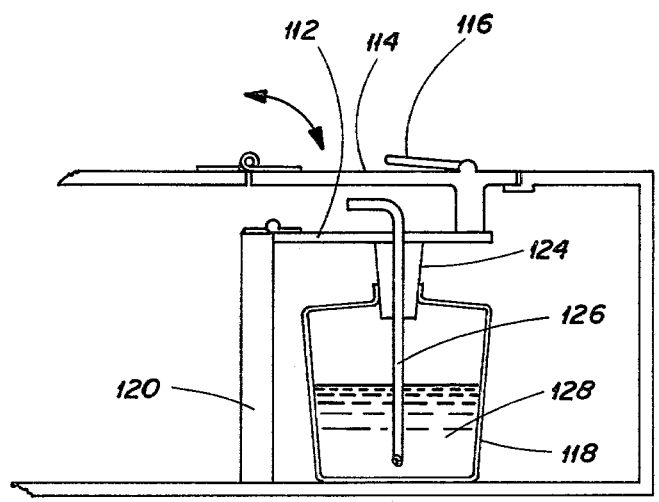
FIG. 7 is a side section, partly schematic view illustrating the reservoirs employed in accordance with the present invention.

Upon the full insertion of slide support tray 22 into rack assembly 40, the slide staining sequence commences. The stain composition employed in accordance with the present invention comprises essentially four components, those being, namely, a fixative, a stain, a buffer solution and a rinse solution. The fixative serves to stabilize the sample and facilitate the application of stain. The stain composition serves to provide the appropriate coloration to the sample so that certain artifacts thereof will become visually distinct upon subsequent examination. The buffer solution serves to stabilize the pH of the sample to prevent deterioration thereof responsive to the treatment with the fixative and stain, and the rinse solution merely removes the excess fixative, stain and buffer solutions from the sample, whereby the sample may be dried and subsequently viewed. Referring now to FIG. 5, a flow diagram schematically representing the apparatus of the present invention illustrates the placement of the aforementioned four components of the stain composition in individual containers or reservoirs which are then drawn by means of the pump as illustrated for purpose of dispensing via manifolds 54 and spigots 58. The application of the components of the stain composition as described above must take place sequentially with the application of the fixative being the first step. Accordingly, the pump schematically disclosed in FIG. 5 must draw from each of the reservoirs set forth above in sequence, that is, the fixative must initially be applied, after which the stain, buffer and rinse are dispensed over the slide sample. Thus, each of the primary lines exiting the pump is divided into two secondary lines each terminating in a manifold 54. The relationship of the primary lines, secondary lines and manifolds can be visualized by reference to FIG. 6 comprising a broken perspective view showing four primary lines 78 splitting into eight secondary lines 80 which then enter the rear of rack assembly 40 to become manifolds 54. Each of the manifolds 54 provides, as disclosed earlier, a dispensing spigot 58 for the purpose of dispensing the particular solution over each of the respective slides 38.

In accordance with the foregoing, the first composition applied to the slides comprises the fixative, followed by the stain and buffer. Referring to FIG. 3, the slide shelf 28 remains in the horizontal position as illustrated therein during the application of these first three solutions. Also, during this time, blower 66, comprising part of the stain composition removal and drying means, directs a gentle stream of air over the slides to assist in the mixing of the three components of the stain composition. During the sequence, the stream must be relatively gentle so as not to drive the components of the stain composition away from the sample, or to otherwise disturb the proper staining thereof. Control of blower pressure may be achieved by a variety of means, such as by electric motor speed control. A venting means is illustrated comprising a secondary air channel 82 provided in rack assembly 40 between support plate 68 and buffer plate 62. Air channel 82 is automatically opened by the action of solenoid 84 on L-shaped pivotable door 86 responsive to the commencement of the staining sequence. As soon as the buffer application sequence is completed, solenoid 84 is released causing door 86 to spring back into closed position whereby full pressure is obtained from blower 66.

In conjuction with the application of full blower pressure as set forth above, the completion of the application of the buffer solution to the slides signals the commencement of the rinsing and drying sequence. It is at this time that slide shelf 28 is urged into the upward canted positioned illustrated in FIG. 4 by the action of lift cam 88, positioned distally with respect to axle 30 holding shelf 28 in position within frame 24. Cam 88 is connected along cam shaft 90 to timing gear housing 92 which is in turn actuated by motor 94, all in response to an electrically timed sequence shown by electrical actuation and control means not illustrated herein. Thus, upon the rotation of cam 88 into the position shown in FIG. 4, the rinse solution is applied via spigot 68 to the slides to facilitate the removal of the fixative, stain and buffer solutions therefrom. Subsequent to the completion of the dispensing of the rinse solution, the blower 66 continues to exert a high pressure stream of air against the slides to drive off the excess stain composition which, as discussed with respect to FIG. 2, passes between the slides 38 as well as through minor openings 34, and is collected within sump 76. Drying continues to completion signalled by a moisture sensor not shown, whereupon an outer light signal indicates the completion of the staining cycle.

In general, the apparatus of the present invention operates through a staining cycle of approximately six minutes commencing with the insertion of slide tray 22 and ending with the signal that the slides are dry. Insofar as the insertion and removal of the slide tray is manually accomplished, the apparatus of the present invention is best described as providing for the semi-automated staining of biological slide samples. In distinction to the prior art devices described earlier, the present invention retains the slides in stationary position upon the slide tray throughout the sequence and thereby avoids the difficulties frequently encountered when the slides are caused to move through the apparatus during the application of the various stain compositions.

In addition to the above, the apparatus of the present invention also includes means for individually staining a single slide. Referring again to FIG. 4, individually slide staining apparatus is shown adjacent rack assembly 40 and comprises secondary rack assembly 96, which is provided in all respect with the same features disclosed respecting rack assembly 40. Thus, rack assembly 96 defines a plurality of tracks adapted to support a screen 98, a diffuser 100 supporting therebelow a single bank of four manifolds 102 identical to manifolds 54, including spigots 104 shown thereon. Above diffuser 100 baffle 106 is provided which varies from baffle 62 in the provision of a shutter-like, solenoid actuated air control 108 which may serve in like manner to secondary air channel 82 to control the magnitude of air pressure allowed to contact the slides. Above baffle 106 reside a secondary support plate 110 which supports a secondary blower 112 which operates in the same manner as blower 66 to direct air over the sample. Also, as with blower 66, blower 112 in the alternative be provided with a speed control to vary the intensity of the air pressure exerted over the slide.

As indicated earlier with respect to FIG. 1, single slide tray 16 is slidably connected to rack assembly 96 and is thereby able to reciprocate into and out of full insertion within rack assembly 96 in the same manner as slide tray 22 operates with respect to rack assembly 40. Single slide tray 16 is beveled out to accommodate the seating of a single slide and cannot be removed from contact with the track of rack assembly 96. Unlike the apparatus for staining a plurality of slides, the single slide staining embodiment employs no tilt mechanism to assist in slide drain off. Slide tray 16 thus remains in fixed horizontal position throughout the staining sequence and relies upon the strength of air pressure generated by blower 112 for the removal of excess stain solution. Slide staining occurs throughout the same sequence as with the multiple slide apparatus including the time frame of the staining sequence.

As indicated earlier, the slide staining apparatus of the present invention, comprising the multiple and single staining apparatus assemblies, is characterized by the total independence of the two assemblies except for the common reliance on stain composition reservoirs. Referring now to FIG. 5, it can be seen that the common reservoirs for fixative, stain, buffer and rinse are provided with separate lines for each of the stain assemblies. Thus, a separate set of lines can be seen from each of the reservoirs going to a pump located above theose reservoirs in FIG. 5 out of which pump four primary lines are directed to the single slide staining apparatus. In this manner, the systems are able to draw upon a common composition supply without the complication of coordinating the supply of two separate systems.

Referring to FIG. 1, a portion of the apparatus of the present invention is provided for the placement of the stain composition reservoirs. Thus, outer housing door 114 is provided which may have a handle 116 for access to an inner compartment which holds the reservoir 118. Reservoir 118 is held in fixed stopper position by means of retainer 120, connected at one end thereof to the base of the apparatus and at the other end thereof to a hingable stopper assembly 122. Stopper assembly 122 comprises a planar member having affixed to one side thereof a stopper structure 124. A cannulus 126 is provided which passes through stopper assembly 122 and stopper 124 to contact the stain composition contained within the reservoir 118. Cannulus 126 extends in the other direction to mate with a wide-type connector, not shown, which splits the fluid path of the cannulus into two paths for channels directed to the respective pumps for each of the staining assemblies comprising the present apparatus.

Securement of the reservoir 118 within the apparatus of the present invention is easily accomplished by first opening door 114, then exerting upward tension on stopper assembly 122 to disengage stopper assembly 112 from the mouth of reservoir 118. Reservoir 118 is then removed and replaced and stopper assembly 122 is lowered into engagement with the mouth thereof. Cannulus 126 is made of a flexible material which prevent damage or breakage that may occur during this procedure. After securement, the stopper assembly 122 within the mouth of reservoir 118, door 118 is lowered into place where it can be seen that lock 130 located on the inner side of door 114 serves to firmly retain stopper assembly 122 in position within reservoir 118. Naturally, door 114 is provided with a latch not shown which secures its engagement with the top of the housing of the apparatus of the present invention.

While there have been herein shown and described the preferred embodiments of the present invention, it will be understood that the invention may be embodied otherwise than as herein specifically illustrated or described and that within said embodiment certain changes in the detail and construction, and the form and arrangement of the parts may be made without departing from the underlying idea or principles of this invention within the scope of the appended claims.

What is claimed is:

1. An apparatus for the staining of a plurality of biological slides which comprises:
    a slide support tray adapted to hold a plurality of slides in parallel position adjacent each other,
    a support tray rack assembly adapted to slidably receive said support tray, said rack assembly including a stain composition dispensing assembly providing a plurality of dispensing spigots, said spigots mounted on said rack assembly in overhead relation to said support tray when said support tray is fully received within said rack assembly, and
    means for removing excess stain composition and drying said slides,
    wherein said support tray is adapted for removable insertion and securement within said rack assembly and comprises a generally rectangular outer tray frame defining a central rectangular aperture therein, a rectangular slide shelf adapted to nest within said aperture and hingably associated with said aperture along at least one side thereof, a plurality of seats defined within said shelf for the parallel disposition thereon of said slides, and said slide shelf is adapted to pivot in relation to said frame in a plane transverse to the direction of insertion of said slide support tray into said rack assembly.

2. The apparatus of claim 1 further including a single slide staining apparatus comprising a reciprocable slide support tray slidably connected to a separate rack assembly, said rack assembly having dispensing means, air blowing means, and a sump for collecting excess stain composition connected therewith.

3. The apparatus of claim 1 wherein said slide shelf defines paired, parallel, rectangular openings of alternating width, comprising openings of greater width adapted to support said slides and openings of lesser width adapted to receive excess stain composition runoff.

4. The apparatus of claim 1 wherein said slide support tray rack assembly comprises a rectangular container defining a plurality of paired, parallel tracks, said tracks adapted to receive said slide support tray, a portion of said dispensing assembly immediately thereabove and means for removing excess stain composition and drying said slides located above said dispensing assembly.

5. The apparatus of claim 4 wherein said rack assembly further includes a screen member insertable below said slide support tray adapted to catch slides accidentally slipping out of engagement therewith.

6. The apparatus of claim 1 wherein said means for removing excess stain composition and drying said slides comprises a rotatable cam member adapted to exert an upward lifting pressure on said slide shelf, and an air blower attached to said rack assembly located at the top thereof adapted to circulate air downward onto said slide.

7. The apparatus of claim 1 wherein said dispensing assembly comprises a plurality of stain composition reservoirs in fluid connection with the pumping means, said pumping means adapted to sequentially force fluid from said reservoirs into position within a plurality of manifolds located over said slide.

8. The apparatus of claim 7 wherein said manifolds comprise extended cylindrical structures residing in a horizontal plane directly over said slides, and said spigots comprise hook-shaped tubular structures attached at one end thereof to the uppermost surface of said manifolds and directed at the opposite end thereof toward said slides.

9. The apparatus of claim 4 wherein said rack assembly further includes at the bottom thereof a sump for the collection of excess stain composition.

* * * * *